(12) United States Patent
Lin et al.

(10) Patent No.: US 11,181,594 B2
(45) Date of Patent: Nov. 23, 2021

(54) SYSTEM AND METHOD FOR LOCALLY CORRELATED SPECTROSCOPY FOR ASSESSING MEDICAL DISCORDERS

(71) Applicants: Brigham and Women's Hospital, Inc., Boston, MA (US); Boston Children's Hospital, Boston, MA (US)

(72) Inventors: Alexander Lin, Waban, MA (US); Susan Waisbren, Boston, MA (US)

(73) Assignees: BRIGHAM AND WOMEN'S HOSPITAL, INC., Boston, MA (US); CHILDREN'S MEDICAL CENTER CORPORATION, Boston, MA (US)

( * ) Notice: Subject to any disclaimer, the term of this patent is extended or adjusted under 35 U.S.C. 154(b) by 454 days.

(21) Appl. No.: 15/526,883

(22) PCT Filed: Nov. 13, 2015

(86) PCT No.: PCT/US2015/060683
§ 371 (c)(1),
(2) Date: May 15, 2017

(87) PCT Pub. No.: WO2016/077757
PCT Pub. Date: May 19, 2016

(65) Prior Publication Data
US 2017/0343633 A1 Nov. 30, 2017

Related U.S. Application Data

(60) Provisional application No. 62/078,998, filed on Nov. 13, 2014.

(51) Int. Cl.
*G01N 33/00* (2006.01)
*G01R 33/46* (2006.01)
(Continued)

(52) U.S. Cl.
CPC ..... *G01R 33/4633* (2013.01); *G01N 33/5038* (2013.01); *G01R 33/483* (2013.01);
(Continued)

(58) Field of Classification Search
CPC .................................................. G01R 33/4633
(Continued)

(56) References Cited

U.S. PATENT DOCUMENTS 4,881,032 A 11/1989 Bottomley
6,617,169 B2 * 9/2003 Ke ..................... G01N 33/9426
324/307

(Continued)

OTHER PUBLICATIONS

Waisbren et al. "Improved Measurement of Brain Phenylalanine and Tyrosine Related to Neuropsychological Functioning in Phenylketonuria" JIMD Rep. 2017;34:77-86 (Year: 2017).*
(Continued)

*Primary Examiner* — Christine T Mui
*Assistant Examiner* — Emily R. Berkeley
(74) *Attorney, Agent, or Firm* — Quarles & Brady LLP

(57) ABSTRACT

Systems and methods for analyzing metabolite concentration in a subject using a medical imaging system are provided. The method includes, using a nuclear magnetic resonance (NMR) system, acquiring data from a subject during multiple acquisitions using different echo times for the multiple acquisitions to create a chemical shift domain. The method also includes, using the chemical shift domain, identifying metabolites by at least two chemical shifts and generating a report indicating the metabolites.

18 Claims, 6 Drawing Sheets

(51) Int. Cl.
  *G01R 33/485* (2006.01)
  *G01R 33/483* (2006.01)
  *G01N 33/50* (2006.01)
  *G01N 24/08* (2006.01)
  *G01R 33/465* (2006.01)

(52) U.S. Cl.
  CPC ........... *G01R 33/485* (2013.01); *G01N 24/08* (2013.01); *G01N 2500/10* (2013.01); *G01N 2570/00* (2013.01); *G01R 33/465* (2013.01)

(58) Field of Classification Search
  USPC ......................................................... 436/173
  See application file for complete search history.

(56) References Cited

U.S. PATENT DOCUMENTS

| | | | |
|---|---|---|---|
| 6,873,153 | B2 | 3/2005 | Frydman |
| 7,200,430 | B2 | 4/2007 | Thomas |
| 2013/0078732 | A1* | 3/2013 | Guffey ............... G01N 33/6812 436/173 |
| 2014/0002075 | A1 | 1/2014 | Lin |

OTHER PUBLICATIONS

Govindaraju V, et al. (2000) Proton NMR chemical shifts and coupling constants for brain metabolites. NMR Biomed 13(3):129-153.

International Searching Authority, International Search Report and Written Opinion for PCT/US15/60683, 14 pages, dated Feb. 1, 2016.

Lin Ap, et al. (2015) Changes in the neurochemistry of athletes with repetitive brain trauma: preliminary results using localized correlated spectroscopy. Alzheimers Res Ther 7(1). doi:10.1186/ s13195-015-0094-5.

Provencher, S. (1997) LCModel webpage accessed online at (https://web.archive.org/web/20161212072800/http://s-provencher.com/lcmodel.shtml).

Ramadan S, et al. (2011) Use of in vivo two-dimensional MR spectroscopy to compare the biochemistry of the human brain to that of glioblastoma. Radiology 259:540-549.

* cited by examiner

SYSTEM AND METHOD FOR LOCALLY CORRELATED SPECTROSCOPY FOR ASSESSING MEDICAL DISCORDERS

CROSS-REFERENCE TO RELATED APPLICATIONS

This application represents the national stage entry of PCT International Application PCT/US2015/060683 filed Nov. 13, 2015, which claims benefit of U.S. Provisional Application 62/078,998 filed Nov. 13, 2014, all of which is incorporated herein in its entirety by reference.

STATEMENT REGARDING FEDERALLY SPONSORED RESEARCH

Background

The present disclosure relates to systems and methods for spectroscopeic analysis of subject to assess medical conditions. More particularly, the present disclosure relates to systems and methods for nuclear magnetic resonance spectroscopy and spectroscopic imaging.

Many metabolic disorders that affect the nervous system can be diagnosed and monitored by calculating concentration of certain amino acids in an individual. Traditionally, metabolic disorders are monitored via blood levels of metabolites, but there has always been the suspicion that these levels do not necessarily reflect the amount of these chemicals in the brain. Thus, in many cases blood levels are not reliable in predicting neuropsychological outcomes in these patients.

Accordingly, numerous methodologies have been applied to fields of radiology, electrophysiology, and cognitive neuroscience for evaluating impairments in metabolic disorders. Magnetic resonance spectroscopy ("MRS") is a tool for non-invasively measuring concentrations of specific metabolites in a region of interest (ROI). However, conventional one-dimensional (1D) MRS can struggle to identify amino acids with low concentrations, especially when many metabolites overlap in a reduced chemical shift range (spectral overlap).

It would therefore be desirable to provide systems and methods for identifying specific, clinically-relevant metabolites that affect neurological impairment.

SUMMARY

The present disclosure overcomes the aforementioned drawbacks by providing systems and methods for assessing metabolic status and the efficacy of current and emerging therapies by obtaining multiple spectroscopy data acquisitions at different echo times. As such, multiple chemical shift domains allow for metabolites to be identified by two chemical shifts instead of just one based on scalar coupling of different proton groups. The concentration of the metabolite can therefore be shown in the third dimension.

In accordance with one aspect of the disclosure, a nuclear magnetic resonance (NMR) spectroscopy system is provided. The NMR system includes a static magnetic field system configured to present a static magnetic field about a subject being studied using the NMR system and a radio frequency (RF) system configured to apply an RF field to the subject and to receive NMR data from the subject using a coil array. The NMR system also includes a computer system configured to control the RF system to acquire data from the subject one-dimensional (1D) spectroscopy data and control the RF system to acquire two-dimensional (2D) spectroscopy data from the subject during multiple data acquisitions using different echo times for the multiple acquisitions to create a chemical shift domain. The computer system is further programmed to use the chemical shift domain to identify metabolites by at least two chemical shifts and, using the 1D spectrum data and the identified metabolites, generate a report indicating the an absolute quantification of metabolites.

In accordance with another aspect of the disclosure, a method for analyzing metabolite concentration in a subject using a medical imaging system is provided. The method includes, using a nuclear magnetic resonance (NMR) system, acquiring data from a subject during multiple acquisitions using different echo times for the multiple acquisitions to create a chemical shift domain. The method also includes using the chemical shift domain to identify metabolites at least including tyrosine or phenylalanine by at least two chemical shifts and generating a report indicating the metabolites at least including tyrosine or phenylalanine.

In accordance with yet another aspect of the disclosure, a method is provided for analyzing metabolite concentration in a subject using a medical imaging system. The method includes using a magnetic resonance imaging (MRI) system to acquire one-dimensional (1D) spectroscopy data from a subject and acquire two-dimensional spectroscopy data from the subject during multiple acquisitions using different echo times for the multiple acquisitions to create a chemical shift domain. The method also includes using the chemical shift domain to identify metabolites by at least two chemical shifts and generating a report indicating the metabolites in three dimensions, wherein an absolute concentration of the metabolites is indicated in one dimension.

In accordance with still another aspect of the disclosure, a method is provided for determining absolute quantification of a compound in an in vivo subject using magnetic resonance spectroscopy (MRS). The method includes acquiring spectroscopy data from the in vivo subject using a magnetic resonance (MR) system and determining, from the spectroscopy data, an absolute concentration in the in vivo subject of at least one of phenylalanine (Phe) or tyrosine (Tyr).

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

As described above, there are a variety of disorders that can be diagnosed and/or treatment can benefit from laboratory or other pathological information related to the presence and/or concentration of certain amino acids in the patient. For example, Phenylketonuria (PKU) is a genetic disorder that results in elevated levels of phenylalanine (Phe) in blood and brain and reduced levels of dopamine (a metabolite of tyrosine) in the brain. It results in progressive neurological decline and mental retardation that can be prevented with a special, protein-restricted diet, and is now routinely tested for in newborn blood tests. While high levels of Phe in the blood is an adequate initial diagnostic, studies have shown discrepancies between measured levels of Phe in blood and those in brain tissue, likely due to individual differences in the amount of the amino acid that crosses the blood-brain barrier. Of great concern, neurological impairment is directly related to levels of Phe in the brain. Studies have revealed that white matter alterations correlate with brain Phe and several untreated patients with normal IQ had lower levels of brain Phe despite high blood Phe levels. Thus, more sensitive tests of brain Phe concentration are needed to monitor progression of the disease and success of treatment. Of course, this is but one example and many other disorders or conditions could likewise benefit form improved or new analysis, diagnosis, or monitoring systems and methods.

Figure 1:
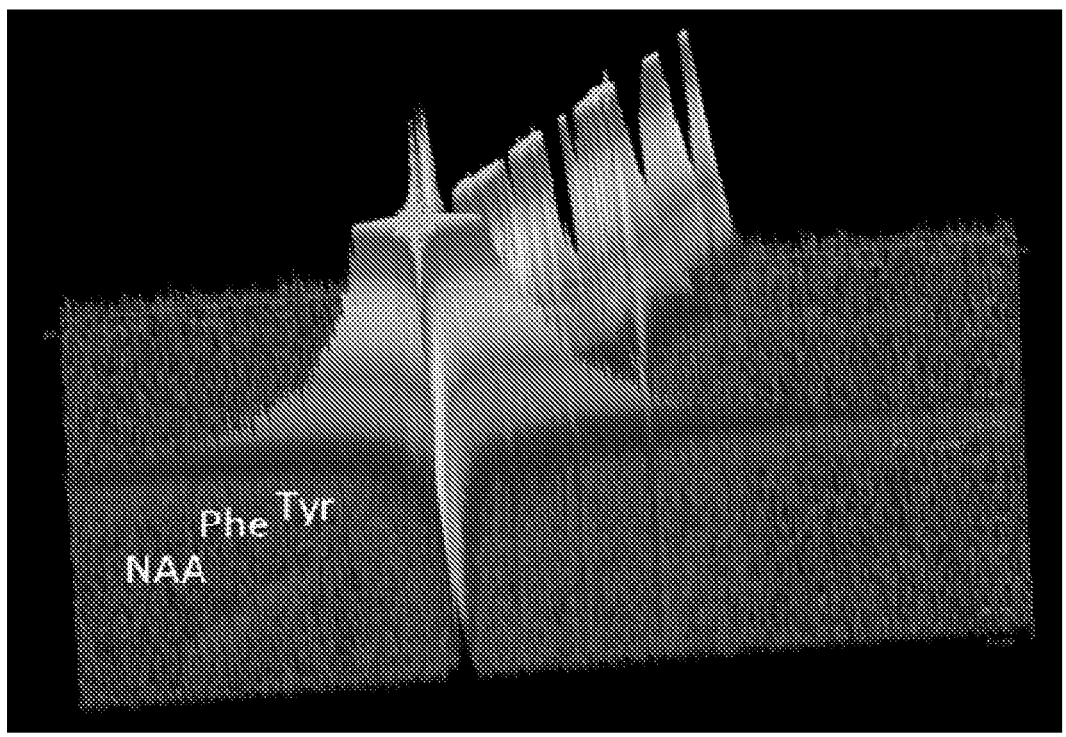
FIG. 1 is an illustration of the 3D spectrum generated from 2D COSY (with metabolite concentration as the third dimension).

Two-dimensional shift correlated MR Spectroscopy (COSY) can be used for the unambiguous identification of cerebral metabolites that may not be detected using conventional 1D MRS methods due to spectral overlap. By obtaining multiple acquisitions at different echo times, a second chemical shift domain allows for metabolites to be identified by two chemical shifts instead of just one based on scalar coupling of different proton groups. The concentration of the metabolite can therefore be shown in the third dimension. By visualizing the COSY data in three dimensions, smaller resonances that would have been obscured by larger resonances can be measured as illustrated in FIG. 1. FIG. 1 shows that the amino acids of interest in the given example, Phe and tyrosine (Tyr), appear at a location on the spectra where they would be obscured with conventional MRS methods because of spectral overlap. To this end, a method is provided for determining absolute quantification of a compound in an in vivo subject using magnetic resonance spectroscopy (MRS). The method includes acquiring spectroscopy data from the in vivo subject using a magnetic resonance (MR) system and determining, from the spectroscopy data, a concentration in the in vivo subject of at least one of phenylalanine (Phe) or tyrosine (Tyr). As one non-limiting example, the systems and methods of the present disclosure may be used to determine concentrations of Phe of between 76 mmol per liter and 185 mmol per liter and concentrations of Tyr of between 4.1 mmol per liter and 131 mmol per liter.

Figure 2A:
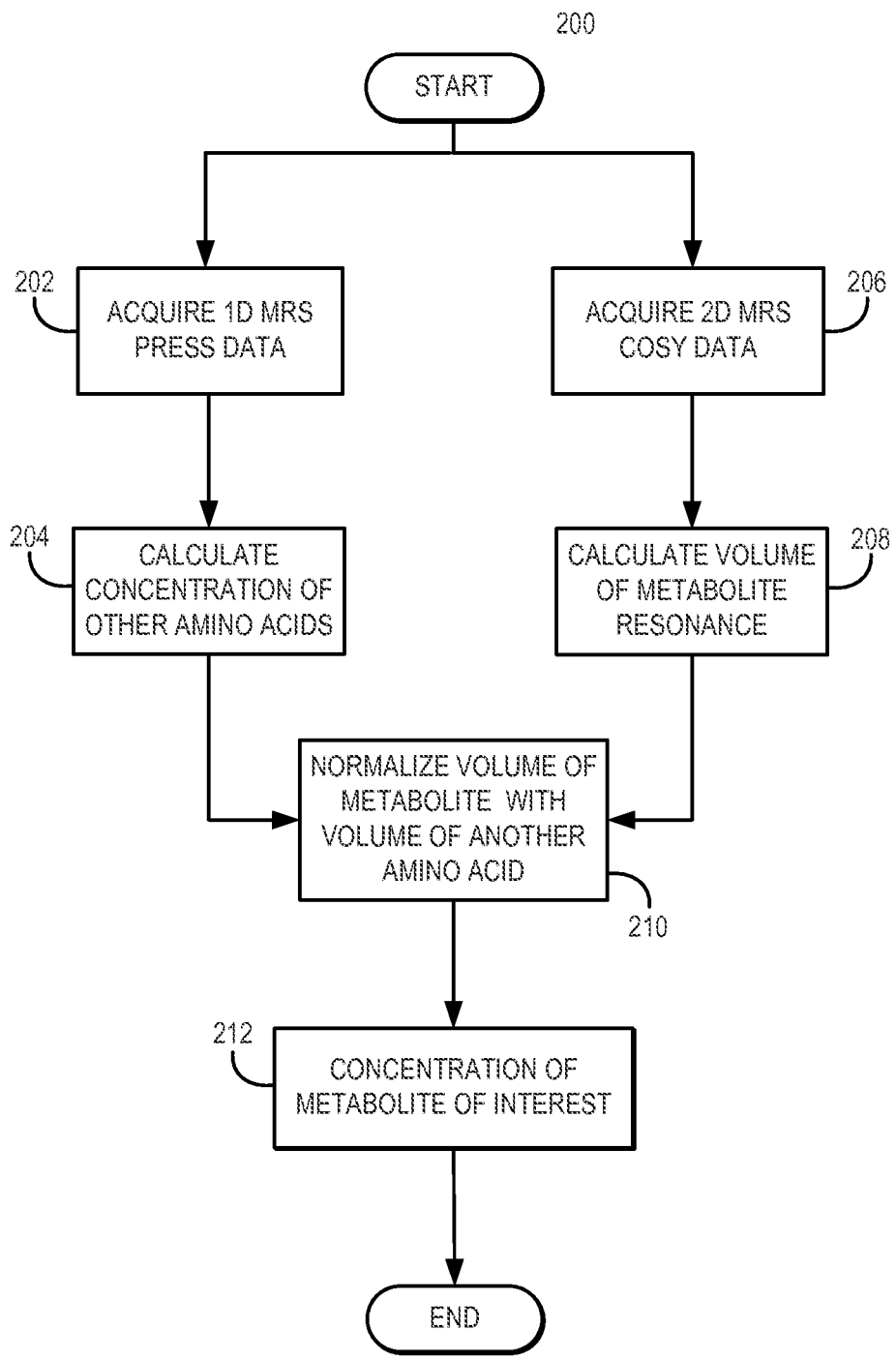
FIG. 2A is a flow chart of the steps performed in accordance with one exemplary implementation of the present disclosure.

Referring to FIG. 2A, a flow chart setting forth the steps of a method 200 for identifying particular amino acids or similar information at concentrations is provided. The process begins at process block 202 where a 1D MRS sequence is used to acquire spectroscopy data from a region of interest (ROI). In one configuration, a PRESS sequence may be used with a repetition time (TR)=2 s and an echo time (TE)=30 ms. By measuring the peak area of their resonances, concentrations of some metabolites can be calculated 204. In some configurations, these metabolites may be NAA, creatine (Cr), Cho, ml, Glu, Gln, GDH, or Lac. In some other configurations, only the area of resonance may be calculated. In other configurations, this can be combined with other MRI data containing information on volume of tissues in the ROI to calculate an absolute concentration of the metabolite.

In series or, as illustrated, in parallel therewith, a 2D COSY sequence may be performed at process block 206 to acquire more spectroscopy data from the same ROI. In one configuration, a COSY sequence may be used with TR=1.5 s and an initial TE of 30 ms with 64 increments of 0.8 ms. From this data, the volume under the resonance of metabolites of interest (that cannot be accurately measured with 1D data) can be measured at process block 208. In process block 210, the volumes of the metabolites of interest are normalized with the volume (or absolute concentration, if known) of an amino acid from process block 204. At process block 212, a relative or absolute concentration of the metabolite of interest within the ROI can be reported. That is a report can be generated at process block 212. The report could be formed as spectroscopy data coupled with anatomical images, textual reports, spectroscopic graphs, or the like.

Figure 2B:
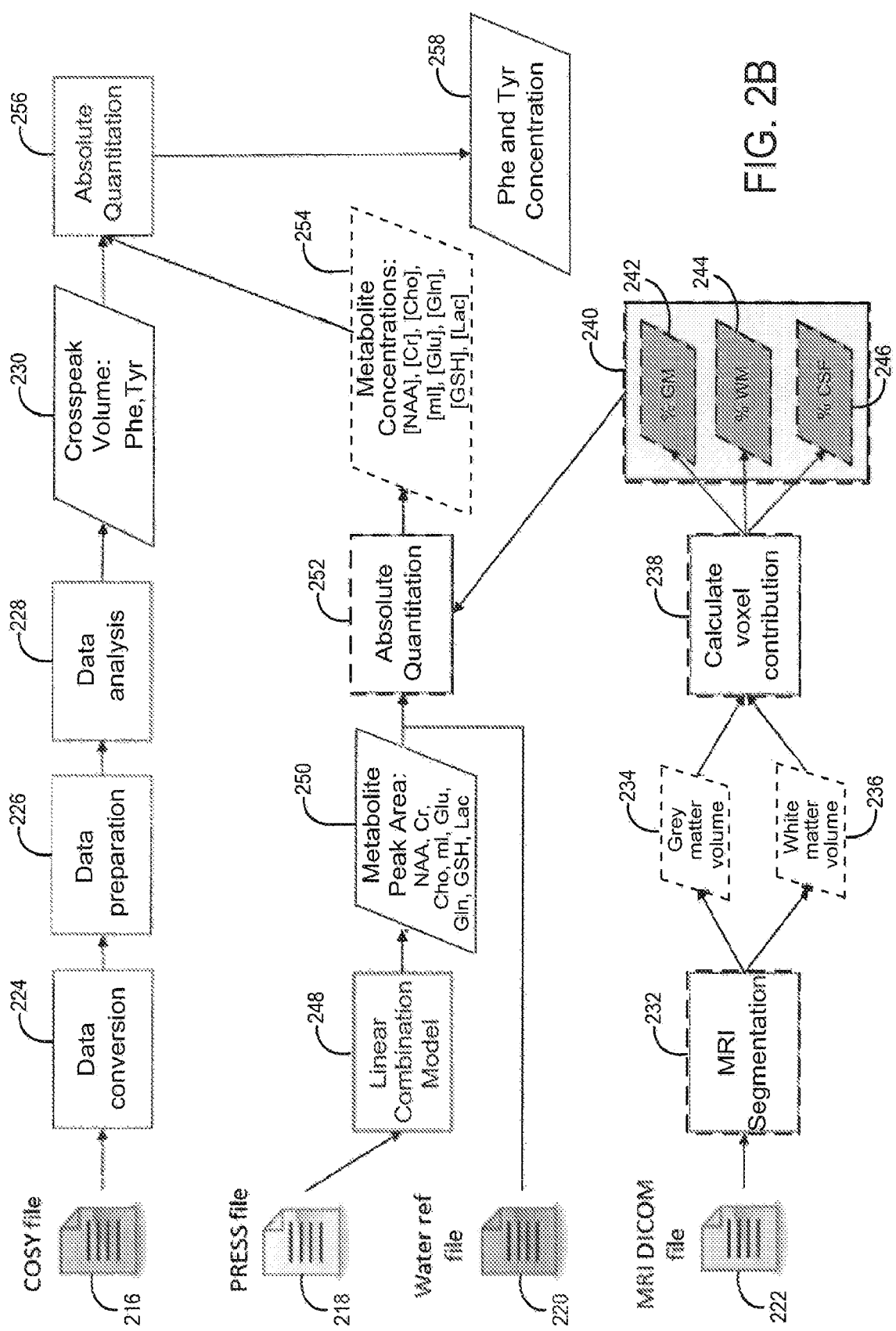
FIG. 2B is a flow chart setting forth some example steps of one particular method for implementing a process in accordance with the present disclosure.

Referring now to FIG. 2B, an example is provided of one particular process for determining metabolite concentration from image data using software developed to implement the process described above with respect to FIG. 2A. The process begins with data from a 2D COSY scan 216, data from a 1D PRESS scan 218, and data from an unsuppressed water reference scan 220. Optionally, a standard MRI scan may also be performed at process block 222 to acquire anatomical imaging data. These data sets 216, 218, 220 and (optionally) 222, may be acquired in any order. The process chain starting with the COSY file 216 and the process chain starting with the 1D PRESS file 218 and the water reference file 220 may be performed in parallel or in series, beginning with either chain, up until process block 256.

Beginning with the COSY data 216, data from the scanner is converted into a format that is compatible with the image processing software at process block 224, and then preprocessing of the data is performed at process block 226 to prepare for analysis. After the data is analyzed in process block 228, the crossing of the peaks from each spectra for a chosen metabolite is located, and the volume of the cross-peak is calculated at process 230. Notably, process block 230 may be performed for one or more chosen metabolites.

The optional process chain starting with process block 222 can be performed in order to obtain absolute, rather than relative, quantitative concentration of the chosen metabolite. The MRI DICOM image file 222 is segmented using image segmentation processes 232 to separate a volume of gray matter (GM) tissue 234 from volume of white matter (WM) tissue 236. These two volume maps can be combined with the region of interest ROI from which the MRS data 216, 218 was acquired, to calculate the contribution of each tissue type to the voxels of the MRI image within the ROI 238. Then, statistics about the region of interest can be calculated at process block 240. For example, the percentage of GM 242, WM 244, and cerebral spinal fluid (CSF) 246 within the volume of the ROI can be calculated. This forms a collection of information about the ROI that may be used later in the overall process.

Regarding the PRESS data 218, a linear combination model can be used at process block 248 to process the 1D PRESS spectrum data 218. The peak from a chosen reference metabolite can be located and the area of the peak is calculated at process block 250. Notably, process block 250 may be performed for one or more metabolites. If the optional data collection is performed at process block 240, the absolute volume of the tissue of interest within the ROI used for spectroscopy is combined with the peak area in the optional process of absolute quantitation 252.

If the optional steps are performed, the result is knowledge of the concentration of the reference metabolite 254. If acquired, this information is combined with the cross-peak volume of the chosen metabolite 230 to perform absolute quantitation of the chosen metabolite at process block 256, to acquire knowledge of the absolute concentration of the chosen metabolite 258 within the ROI. In any case, by combining 2D COSY data 216 with 1D PRESS data, an absolute quantification of the desired metabolites can be achieved 256. That is, unlike methods that employ COSY data and are non-quantitative apart from relative measures to a given metabolite, such as creatine, the systems and methods of the present disclosure can provide absolute concentration of the chosen metabolite 258.

If the optional data from process block 240 has not been obtained, process blocks 252 and 254 may be omitted. Then process block 256 is used to combine information from process block 230 with that from process block 250 in a relative quantification. In this case, the result 258 is not an absolute concentration, but the relative concentration expressed as a ratio of the chosen metabolite to the reference metabolite.

Figure 3:
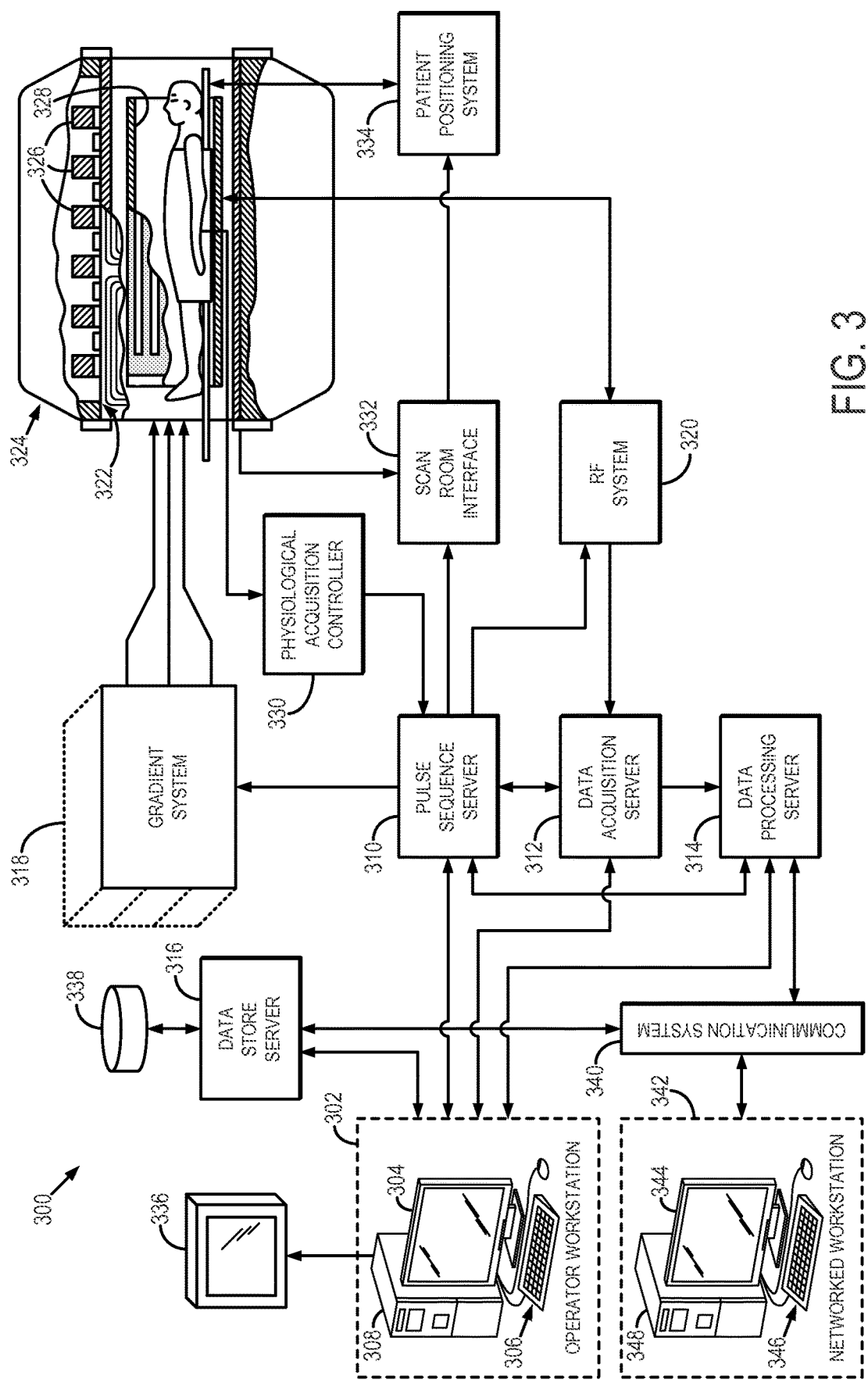
FIG. 3 is a block diagram of an example of a nuclear magnetic resonance ("NMR") system and, in particular, a magnetic resonance imaging ("MRI") system.

To acquire the above-described data, a nuclear magnetic resonance ("NMR") system and, more particularly, a magnetic resonance imaging ("MRI") and/or MRS system, may be used. Referring particularly now to FIG. 3, an example of an NMR system, in this case, an MRI system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \tag{1};$$

and the phase of the received magnetic resonance signal may also be determined according to the following relationship:

$$\varphi = \tan^{-1}\left(\frac{Q}{I}\right). \tag{2}$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

Pulse sequences for use with MRI or MRS systems, such as described above with respect to FIG. 3, that facilitate localized in vivo low-power adiabatic TOCSY and COSY are provided. The sequences allow improved magnetization transfer efficiency, precise localization, and reduced SAR. These sequences can be run in a standard clinical environment with a feasible acquisition time.

Figure 4:
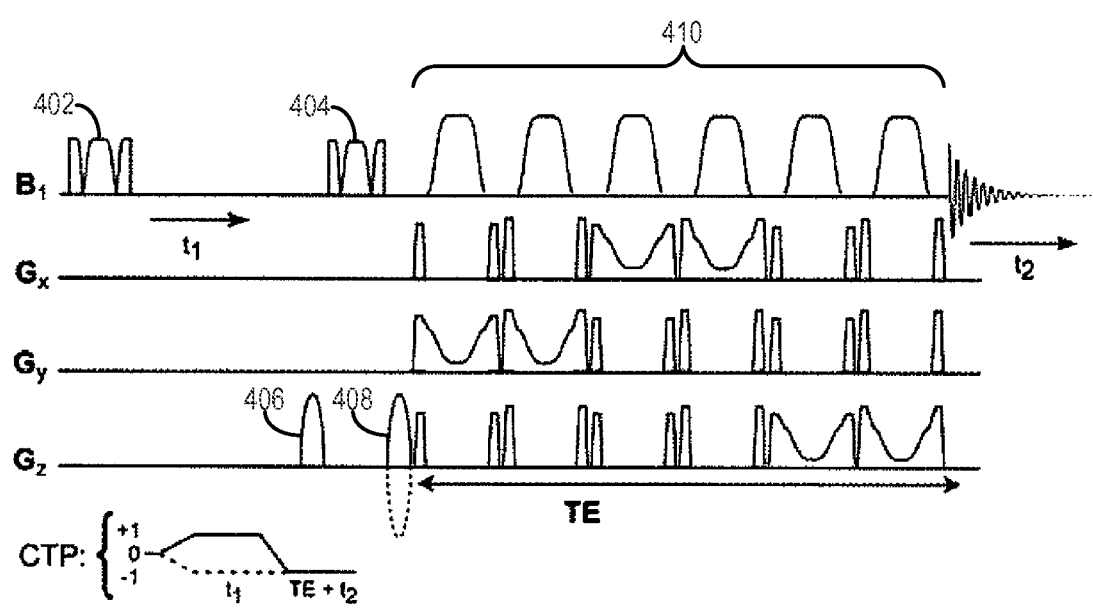
FIG. 4 is a pulse sequence diagram for an example of a fully adiabatic, two-dimensional COSY pulse sequence that uses LASER localization in accordance with an embodiment of the present disclosure.

Referring now to FIG. 4, an example of a fully adiabatic, two-dimensional COSY pulse sequence that uses localized adiabatic selective refocusing ("LASER") localization is illustrated. The pulse sequence includes an RF excitation pulse 402 followed by the application of a ninety degree adiabatic BIR-4 pulse 404 that is bracketed by a first and second CTP gradient 406, 408. Following the application of the second CTP gradient 408, a LASER localization module 410 is performed. The polarity of the CTP gradients 406, 408 can be alternated for interleaved echo-antiecho acquisitions.

Figure 5A:
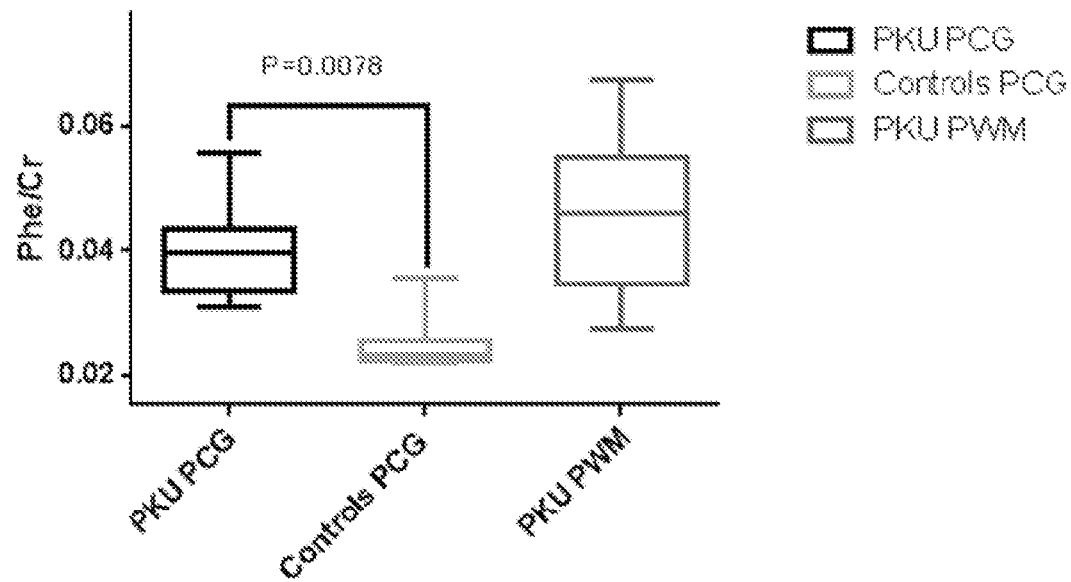
FIG. 5 is a chart showing the quantitative results of one exemplary implementation of the present disclosure.

Using a COSY pulse sequence, such as described above, experiments were performed to obtain quantifiable measurements of Phe in the brain. From the experiments, posterior Cingulate Phe levels (0.039+0.0076; range=0.03 to 0.06) were significantly higher than that of controls (0.025+0.004; range=0.022 to 0.036 $p<0.01$) as shown in FIG. 5A. Turning now to FIG. 5A, a graph is provided that summarizes results from an example experiment looking at Phe in PKU. As illustrated in FIG. 5, the systems and methods can be used to acquire Phe/Cr concentrations in the PCG and PWM. As illustrated, there was significant difference between controls and PKU in the PCG, but no difference from PWM.

Thus, the PKU PWM Phe levels (0.045+0.013; range=0.027 to 0.056) were not significantly different from the PKU PCG levels. The correlation between brain Phe biomarkers and neuropsychological functioning directed attention to the importance of accumulation of Phe in the white matter region, as summarized in Table 1.

TABLE 1

Correlation (r) between Phe Biomarkers and Scores on Neuropsychological Tests

|  | IQ | BRIEF (Executive Functioning) | Depression | Anxiety |
| --- | --- | --- | --- | --- |
| Blood Phe | 0.11 | 0.25 | 0.25 | 0.74 |
| 1. Brain Phe PWM | 0.15 | −0.47 | −0.25 | 0.14 |
| 2. Brain Phe PCG | −0.07 | −0.22 | −0.20 | −0.41 |

Figure 5B:
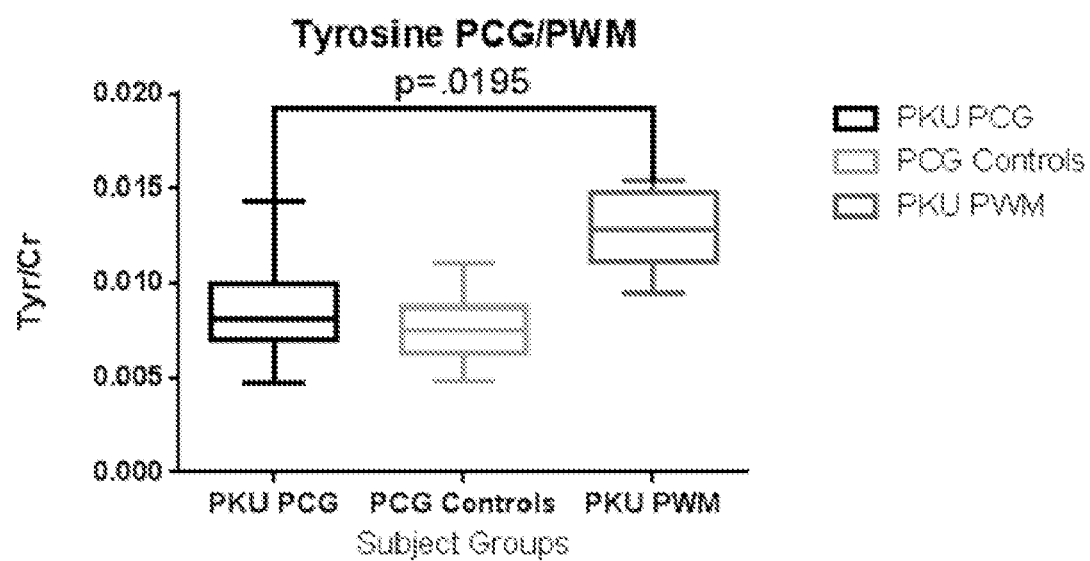

Experiments were also preformed to obtain quantifiable measurements of Tyr in the brain, as well. FIG. 5B shows that Tyr/Cr concentrations in the PCG and PWM can also be studied using the systems and method of the present disclosure. There was significant difference between PKU PCG and PWM, but no difference from controls. Thus, the PKU PCG Tyr levels (0.009+0.003; range=0.005 to 0.014) is was not significantly different from control PCG Tyr levels (0.008+0.002; range=0.005 to 0.011) and the ranges were similar, as well.

Such data supports the findings that elevated phenylalanine levels in plasma result in an increase in Phe levels within brain cells. Using the systems and methods of the present disclosure, it is possible to measure even small elevations in brain with the exactitude. It is also possible to differentiate tyrosine levels in the brain from phe levels in individuals with PKU. Although accumulation of Phe in the brain was similar in the white and gray matter regions examined in the above experiments, only white matter levels were associated with neuropsychological functioning and self-reported levels of anxiety and depression. These studies using the systems and methods of the present disclosure have provided accurate measurements of Phe levels in adults in the general population. The brain Phe levels in individuals with PKU were significantly higher than brain phe levels in controls in grey matter. However, the tyrosine levels were not significantly different between the individuals with PKU and controls in grey matter.

The higher the Phe level within brain tissue, the greater is the perturbation in neuropsychological function, but only within white matter. Since the voxel contains a mixture of cell types such as neuronal cell bodies, axons, oligodendroglia, astrocytes, microglia, pericytes and endothelial cells, an important question is whether the Phe is elevated in all cells to the same degree or only in those that are pathological targets of toxicity. Since the white matter appears to be a selective target with alterations in neuropsychological function being linked with cellular Phe, it is possible that the cellular target is an oligodendroglial cell and/or the axon itself. Thus, the present disclosure provides valuable tools to consider such clinically-relevant issues.

The next important question is whether the toxicity associated with elevated Phe in the oligodendrocyte and/or axon is due to Phe per se or a consequence of increased influx of Phe at LAT-1 with inhibition of other large neutral amino acids such as tyrosine into the cell. In other words, is the toxicity due to a direct effect of Phe in the cell or a nutritional deficiency of one or more large neutral amino acids? In certain cells, a deficiency of tyrosine may lead to impaired dopamine synthesis whereas in others it may simply impair protein synthesis. With the systems and methods provided herein, one can quantify tyrosine as well as other large neutral amino acids in multiple brain regions to consider these and other issues and make additional and new clinical decisions to assist patients at an ever-earlier stage.

Thus, as described above, a clinically viable system and method are provided for measuring brain phenylalanine and extraction of absolute concentrations (millmolar wet weight) that are comparable to blood concentrations. The systems and methods provide a robust MRI and MRS protocol that provides high-quality data and is readily reproducible. The systems and methods can use of the correlated spectroscopy method at 3 Tesla field strengths and post-processing software can be used to automate the quantification of brain phenylalanine concentrations. In addition, the present systems and methods have been demonstrated to measure a variety of amino acids, such as tyrosine, the end product of phenylalanine hydroxylation that is deficient in PKU patients and a precursor to dopamine.

The present disclosure has been described in terms of one or more preferred embodiments, and it should be appreciated that many equivalents, alternatives, variations, and modifications, aside from those expressly stated, are possible and within the scope of the disclosure.

The invention claimed is:

1. A method for analyzing metabolite concentration in a subject using a medical imaging system, the method comprising:
   using a nuclear magnetic resonance (NMR) system, acquiring data from a subject during multiple acquisitions using different echo times for the multiple acquisitions to create a chemical shift domain;
   using the chemical shift domain, identifying metabolites at least including tyrosine or phenylalanine by at least two chemical shifts for each metabolite; and
   generating a report indicating the metabolites at least including tyrosine levels or phenylalanine.

2. The method of claim 1 wherein identifying the metabolites by the at least two chemical shifts corresponding to different proton groups in the subject.

3. The method of claim 1 wherein the report indicates a concentration of the metabolites in three dimensions.

4. The method of claim 1 wherein using the NMR system to acquire the data includes acquiring two-dimensional (2D) spectroscopy data from the subject.

5. The method of claim 4 wherein using the NMR system to acquire the data includes acquiring one-dimensional (1D) spectroscopy data from the subject.

6. The method of claim 5 wherein a concentration of a given metabolite calculated from the 1D spectroscopy data is used as a reference to normalize the 2D spectroscopy data.

7. The method of claim 6 wherein at least one of the 2D spectroscopy data is acquired using a COSY pulse sequence or the 1D spectroscopy data is acquired using a PRESS pulse sequence.

8. The method of claim 1 further comprising acquiring anatomical data of the subject and using the anatomical data to quantify an absolute metabolite concentration in a selected volume within the subject.

9. The method of claim 8 wherein the NMR system includes a magnetic resonance imaging (MRI) system and wherein the anatomical data is acquired using the MRI system.

10. The method of claim 1 wherein the report includes an absolute quantification of the metabolites at least including tyrosine levels or phenylalanine.

11. A method for analyzing metabolite concentration in a subject using a medical imaging system, the method comprising:
    using a magnetic resonance imaging (MRI) system, acquiring one-dimensional (1D) spectroscopy data from a subject;
    using the MRI system, acquiring two-dimensional (2D) spectroscopy data from the subject during multiple acquisitions using different echo times for the multiple acquisitions to create a chemical shift domain;
    using the chemical shift domain, identifying metabolites by at least two chemical shifts for each metabolite; and
    generating a report indicating the metabolites in three dimensions, wherein an absolute concentration of the metabolites is indicated in one dimension.

12. The method of claim 1, further comprising using a nuclear magnetic resonance (NMR) system, to acquire one-dimensional (1D) spectroscopy data from a subject.

13. The method of claim 12 wherein acquiring the 1D spectroscopy data includes performing a first pulse sequence using the MRI system and acquiring the 2D spectroscopy data includes performing a second pulse sequence using the MRI system, wherein the first pulse sequence and the second pulse sequence are different pulse sequences.

14. The method of claim 13 wherein the second pulse sequence includes a two-dimensional shift correlated MR spectroscopy (COSY) pulse sequence.

15. The method of claim 1 wherein using the chemical shift domain to identify metabolites at least including tyrosine or phenylalanine by at least two chemical shifts for each metabolite includes assessing a concentration of the metabolite in a third dimension of the chemical shift domain.

16. The method of claim 11 wherein acquiring the 1D spectroscopy data includes performing a first pulse sequence using the MRI system and acquiring the 2D spectroscopy data includes performing a second pulse sequence using the MRI system, wherein the first pulse sequence and the second pulse sequence are different pulse sequences.

17. The method of claim 16 wherein the second pulse sequence includes a two-dimensional shift correlated MR spectroscopy (COSY) pulse sequence.

18. The method of claim 11 wherein using the chemical shift domain to identify metabolites at least including tyrosine or phenylalanine by at least two chemical shifts for each metabolite includes assessing a concentration of the metabolite in a third dimension of the chemical shift domain.

* * * * *

UNITED STATES PATENT AND TRADEMARK OFFICE
CERTIFICATE OF CORRECTION

PATENT NO. : 11,181,594 B2
APPLICATION NO. : 15/526883
DATED : November 23, 2021
INVENTOR(S) : Alexander Lin et al.

Page 1 of 1

It is certified that error appears in the above-identified patent and that said Letters Patent is hereby corrected as shown below:

On the Title Page

Item (54), in the title, "DISCORDERS" should be --DISORDERS--.

In the Specification

Column 1, Line 3, "DISCORDERS" should be --DISORDERS--.

Signed and Sealed this
Thirty-first Day of May, 2022

Katherine Kelly Vidal
*Director of the United States Patent and Trademark Office*